US006881815B2

(12) United States Patent
Odle et al.

(10) Patent No.: US 6,881,815 B2
(45) Date of Patent: Apr. 19, 2005

(54) METHOD FOR THE PREPARATION POLY (ETHERIMIDE)S

(75) Inventors: Roy Ray Odle, Mt. Vernon, IN (US); Thomas Link Guggenheim, Mt. Vernon, IN (US)

(73) Assignee: General Electric Company, Pittsfield, MA (US)

( * ) Notice: Subject to any disclaimer, the term of this patent is extended or adjusted under 35 U.S.C. 154(b) by 16 days.

(21) Appl. No.: 10/065,197

(22) Filed: Sep. 25, 2002

(65) Prior Publication Data

US 2004/0063897 A1 Apr. 1, 2004

(51) Int. Cl.$^7$ .................. C08G 73/10; C08G 69/28; C08G 69/26; C07D 209/48
(52) U.S. Cl. .................. 528/170; 528/125; 528/126; 528/128; 528/171; 528/172; 528/173; 528/174; 528/176; 528/179; 528/183; 528/185; 528/188; 528/220; 528/229; 528/350; 528/351; 528/353; 548/461; 549/241; 549/248
(58) Field of Search .................. 528/125, 126, 528/128, 170–174, 176, 179, 183, 185, 188, 220, 229, 350, 351, 353; 548/461, 485; 549/241, 248

(56) References Cited

U.S. PATENT DOCUMENTS

| | | | |
|---|---|---|---|
| 1,891,843 A | 12/1932 | Shaw et al. | |
| 2,391,226 A | 12/1945 | Clifford et al. | |
| 2,764,597 A | 9/1956 | Barney | |
| 3,240,792 A | 3/1966 | Patrick et al. | |
| 3,346,597 A | 10/1967 | Acetis | |
| 3,480,667 A | 11/1969 | Siegart et al. | |
| 3,506,689 A | 4/1970 | Peterlein | |
| 3,803,085 A | 4/1974 | Takehoshi et al. | |
| 3,819,658 A | 6/1974 | Gormley et al. | |
| 3,847,869 A | 11/1974 | Williams | 528/170 |
| 3,850,965 A | 11/1974 | Williams, III | |
| 3,875,116 A | 4/1975 | Heath et al. | |
| 3,879,428 A | 4/1975 | Heath et al. | |
| 3,941,883 A | 3/1976 | Gschwend et al. | |
| 3,965,125 A | 6/1976 | Meyers | |
| 3,972,902 A | 8/1976 | Heath et al. | |
| 3,983,093 A | 9/1976 | Williams, III et al. | |
| 3,989,712 A | 11/1976 | Williams, III | |
| 4,005,134 A | 1/1977 | Markezich | |
| 4,045,408 A | 8/1977 | Griffith et al. | |
| 4,054,600 A | 10/1977 | Johnson | |
| 4,217,281 A | 8/1980 | Markezich et al. | |
| 4,247,464 A | 1/1981 | Relles et al. | |
| 4,257,953 A | 3/1981 | Williams, III et al. | |
| 4,273,712 A | 6/1981 | Williams, III | |
| 4,289,781 A | 9/1981 | Bengtsson et al. | |
| 4,302,396 A | 11/1981 | Tsujimoto et al. | |
| 4,318,857 A | 3/1982 | Webb et al. | |
| 4,329,291 A | 5/1982 | Webb et al. | |
| 4,329,292 A | 5/1982 | Webb | |
| 4,329,496 A | 5/1982 | Webb | |
| 4,340,545 A | 7/1982 | Webb et al. | |
| 4,374,267 A | 2/1983 | Fifolt et al. | |
| 4,417,044 A | 11/1983 | Parekh | |
| 4,455,410 A | 6/1984 | Giles, Jr. | |
| 4,489,185 A * | 12/1984 | Schoenberg | 524/104 |
| 4,514,572 A | 4/1985 | Hamprecht et al. | |
| 4,517,372 A | 5/1985 | Tang | |
| 4,520,204 A | 5/1985 | Evans | |
| 4,543,416 A | 9/1985 | Peters | |
| 4,559,405 A | 12/1985 | Telschow | |
| 4,560,772 A | 12/1985 | Telschow et al. | |
| 4,560,773 A | 12/1985 | Telschow | |
| 4,571,425 A | 2/1986 | Silva | |
| 4,578,470 A * | 3/1986 | Webb | 546/256 |
| 4,584,388 A | 4/1986 | Webb | |
| 4,599,396 A * | 7/1986 | Takekoshi et al. | 528/185 |
| 4,599,429 A | 7/1986 | Odle | |
| 4,612,361 A | 9/1986 | Peters | |
| 4,634,760 A * | 1/1987 | Takekoshi et al. | 528/353 |
| 4,650,850 A | 3/1987 | Howson | |
| 4,675,376 A | 6/1987 | Peters | |
| 4,680,412 A | 7/1987 | Hamprecht et al. | |
| 4,827,000 A | 5/1989 | Schwartz | |
| 4,864,034 A | 9/1989 | Cella et al. | |
| 4,868,316 A | 9/1989 | Schwartz, Jr. | |
| 4,902,809 A | 2/1990 | Groeneweg et al. | |
| 4,921,970 A | 5/1990 | Odle | |
| 4,960,905 A | 10/1990 | Schwartz | |
| 4,962,206 A | 10/1990 | Cocoman et al. | |
| 4,965,337 A | 10/1990 | Peters et al. | |
| 4,978,760 A | 12/1990 | Spohn | |
| 5,003,088 A | 3/1991 | Spohn et al. | |
| 5,021,588 A | 6/1991 | Contractor | |
| 5,049,682 A | 9/1991 | Tang et al. | |
| 5,059,697 A | 10/1991 | Fertel et al. | |
| 5,082,968 A | 1/1992 | Brunelle | |
| 5,132,423 A | 7/1992 | Brunelle et al. | |
| 5,155,234 A | 10/1992 | Odle | |

(Continued)

FOREIGN PATENT DOCUMENTS

EP    1 059 291 A    12/2002

OTHER PUBLICATIONS

JP 10237063. Publication Date Sep. 9, 1998. English Abstract.

*Primary Examiner*—P. Hampton Hightower

(57) ABSTRACT

A method for the synthesis of poly(etherimide)s comprises the reaction of 4-halotetrahydrophthalic anhydride with an activating primary amine to yield an activated 4-halotetrahydrophthalimide. Activated 4-halotetrahydrophthalimide may then be aromatized and treated with the disodium salt of a bis(phenol) to yield an activated bisimide. The activated bisimide may then be directly treated with a diamine to yield poly(etherimide)s.

41 Claims, No Drawings

U.S. PATENT DOCUMENTS

| | | |
|---|---|---|
| 5,185,451 A | 2/1993 | Stults et al. |
| 5,206,391 A | 4/1993 | Seper et al. |
| 5,223,054 A | 6/1993 | Yoshimoto |
| 5,229,482 A | 7/1993 | Brunelle |
| 5,233,054 A | 8/1993 | Tang et al. |
| 5,235,071 A | 8/1993 | Ueda et al. |
| 5,266,678 A | 11/1993 | Perry et al. |
| 5,300,201 A | 4/1994 | Seper et al. |
| 5,322,954 A | 6/1994 | Seper et al. |
| 5,359,084 A | 10/1994 | Dellacoletta et al. |
| 5,359,092 A | 10/1994 | Hay et al. |
| 5,364,824 A | 11/1994 | Andrews et al. |
| 5,459,227 A | 10/1995 | Hay et al. |
| 5,510,308 A | 4/1996 | Kourtakis |
| 5,536,846 A | 7/1996 | Dellacoletta et al. |
| 5,557,005 A | 9/1996 | Semler et al. |
| 5,672,750 A | 9/1997 | Perry |
| 5,683,553 A | 11/1997 | Baur et al. |
| 5,705,685 A | 1/1998 | Lyons et al. |
| 5,719,295 A | 2/1998 | Dellacoletta et al. |
| 5,750,777 A | 5/1998 | Aubry et al. |
| 5,779,792 A | 7/1998 | Atami et al. |
| 5,792,719 A | 8/1998 | Eberle et al. |
| 5,830,974 A | 11/1998 | Schmidhauser et al. |
| 5,872,294 A | 2/1999 | Caringi et al. |
| 5,908,915 A | 6/1999 | Brunelle |
| 5,936,099 A | 8/1999 | Dellacoletta et al. |
| 6,008,374 A | 12/1999 | Dellacoletta et al. |
| 6,011,122 A | 1/2000 | Puyenbroek |
| 6,072,010 A | 6/2000 | Puyenbroek |
| 6,235,866 B1 * | 5/2001 | Khouri et al. ............... 528/125 |
| 6,265,521 B1 * | 7/2001 | Fyvie et al. ................ 528/170 |
| 6,498,224 B1 * | 12/2002 | Odle et al. ................. 528/170 |
| 6,528,663 B1 | 3/2003 | Odle et al. ................. 549/246 |
| 6,576,770 B1 * | 6/2003 | Odle et al. ................. 548/485 |
| 6,590,108 B1 * | 7/2003 | Odle et al. ................. 549/241 |
| 6,710,187 B1 * | 3/2004 | Guggenheim et al. ...... 549/241 |

* cited by examiner

METHOD FOR THE PREPARATION POLY(ETHERIMIDE)S

BACKGROUND OF INVENTION

This invention relates to a method for the manufacture of poly(etherimide)s. More particularly, it relates to a method for the manufacture of poly(etherimide)s which eliminates the need for nitration.

Polyetherimides are high heat engineering plastics having a variety of uses. The present commercial process for the synthesis of polyetherimides requires nitration of N-methylphthalimide to yield 4-nitro-N-methylphthalimide. 4-nitro-N-methylphthalimide is treated with the disodium salt of a bis(phenol) such as bisphenol A to yield a bisimide (I) having the following general structure:

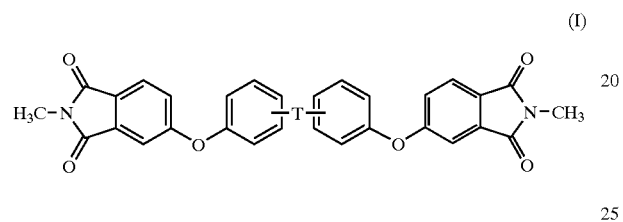
(I)

Bisimide (I) is then reacted with a phthalic anhydride in an exchange reaction to yield the dianhydride (II):

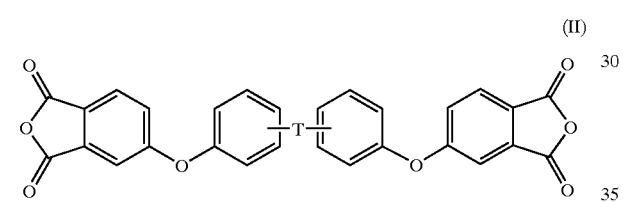
(II)

Reaction of dianhydride (II) with a diamine results in polymerization to a poly (etherimide). Methods which improve or even eliminate any of the preceding steps would result in an improved synthesis of polyetherimides.

SUMMARY OF INVENTION

A new method for the synthesis of polyetherimides comprises reaction of 4-halotetrahydrophthalic anhydride (III)

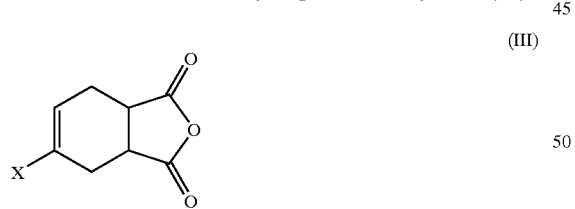
(III)

with an activating primary amine having the formula A-NH$_2$ to yield N-substituted-4-halotetrahydrophthalimide (IV)

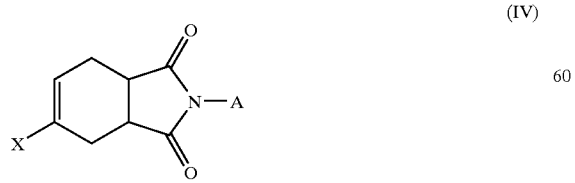
(IV)

wherein A is a group which activates the tetrahydrophthalimide ring system to aromatization. N-substituted-4-halotetrahydrophthalimide (IV) is aromatized to yield N-substituted-4-halophthalimide (V):

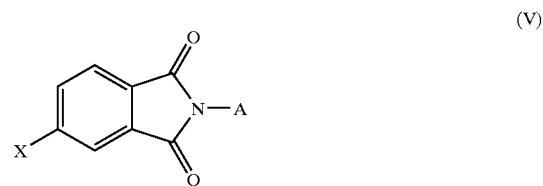
(V)

N-substituted-4-halophthalimide (V) may then be treated with the disodium salt of a dihydroxy compound to yield the activated bisimide (VI):

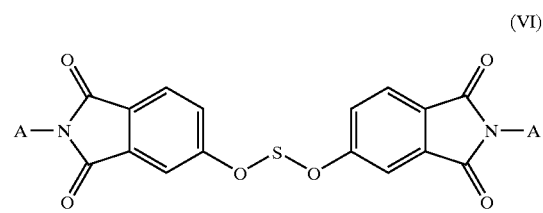
(VI)

Activated bisimide (VI) may then be directly treated with a diamine (VII) having the structure

$$H_2N\text{-}Z\text{-}NH_2 \qquad (VII)$$

to yield poly(etherimide)s and the activating primary amine.

In another embodiment, a method for the synthesis of polyetherimides comprises the reaction of 4-halotetrahydrophthalic anhydride (III)

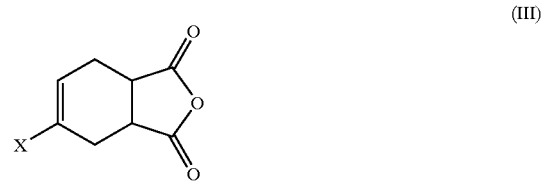
(III)

with an activating primary amine having the formula A-NH$_2$ to yield N-substituted-4-halotetrahydrophthalimide (IV)

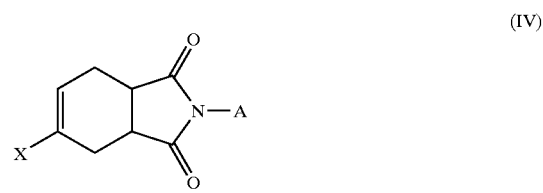
(IV)

wherein A is a group which activates the tetrahydrophthalimide ring system to aromatization. N-substituted-4-halotetrahydrophthalimide (IV) is aromatized to yield N-substituted-4-halophthalimide (V):

N-substituted-4-halophthalimide (V) may then be treated with the disodium salt of a dihydroxy compound to yield the activated bisimide (VI):

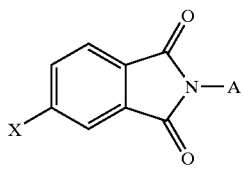
(V)

(VI)

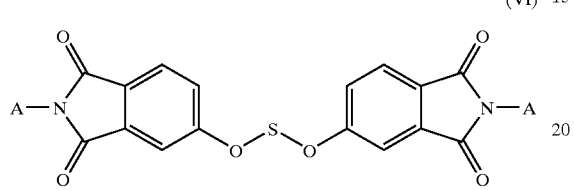

Activated bisimide (VI) is then treated with phthalic anhydride or hydrolysis ring closure to yield dianhydride (VIII):

(VIII)

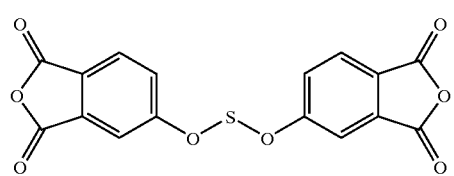

Dianhydride (VIII) may then be reacted with diamine (VII) to yield poly(etherimide).

In another embodiment, a method for the synthesis of polyetherimides comprises the reaction of 4-halotetrahydrophthalic anhydride (III)

(III)

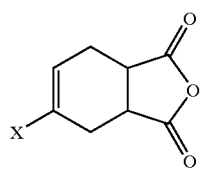

with an activating primary amine having the formula A-NH$_2$ to yield N-substituted-4-halotetrahydrophthalimide (IV)

(IV)

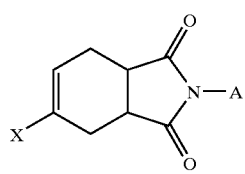

wherein A is a group which activates the tetrahydrophthalimide ring system to aromatization. N-substituted-4-halotetrahydrophthalimide (IV) is aromatized to yield N-substituted-4-halophthalimide (V):

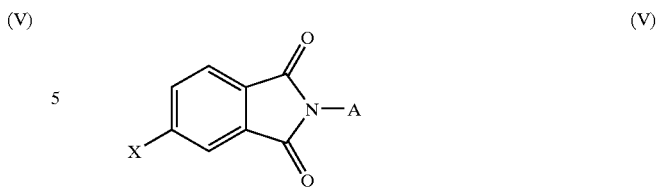
(V)

N-substituted-4-halophthalimide (V) may then be treated with diamine (VII) in a transimidation facilitated by the presence of the activating group A to produce the dihalobisimide (IX)

(IX)

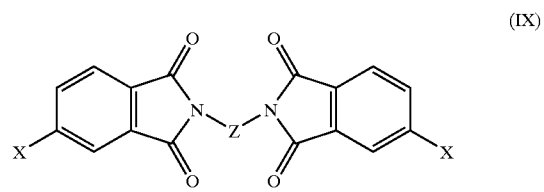

Dihalobisimide (IX) can be reacted with the disodium salt of a dihydroxy compound to yield poly(etherimide).

DETAILED DESCRIPTION

The reaction of 4-halotetrahydrophthalic anhydride (III)

(III)

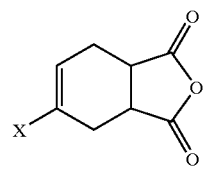

wherein X is a halogen, preferably chlorine, with an activating primary amine results in N-substituted-4-halotetrahydrophthalimide. 4-halotetrahydrophthalic anhydride (III) may be obtained by the Diels-Alder condensation of maleic anhydride with 2-halo-1,3-butadiene as disclosed in U.S. Pat. No. 5,003,088 to Spohn.

Suitable activating primary amines have the structure A-NH$_2$, wherein A is a group effective to activate the tetrahydrophthalimide ring system to aromatization. Suitable activating groups include, but are not limited to, pyridyls, chloropyridyls, nitropyridyls, pyrimidine, pyrazine, thiazole, methylthiazole, benzothiazole, 1,3,4-thiadiazole, and benzotriflouride. A preferred activating group is 2-pyridyl. As will be discussed later, the presence of the activating group A can also facilitate transimidization.

The reaction of 4-halo-tetrahydrophthalic anhydride with the activating amine may be conducted without a solvent or in an inert solvent such as acetic acid, ortho-dichlorobenzene, xylene, or toluene. The reaction mixture is heated to a temperature of about 125° C. to about 300° C., preferably about 200° C. to about 275° C. Volatile by-products such as water are typically removed as they are formed. It is usually preferred to carry out the reaction in an inert atmosphere. Approximately equivalent amounts of 4-halotetrahydrophthalic anhydride and activating primary amine are used. The reaction yields an activated 4-halotetrahydrophthalimide (IV):

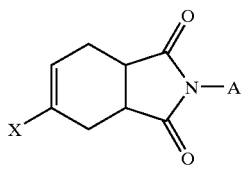

(IV)

wherein A is an activating group as described above.

Activated 4-halotetrahydrophthalimide (IV) is aromatized in the presence of a catalyst to yield N-substituted-4-halophthalimide (V)

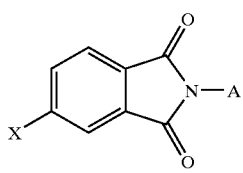

(V)

Appropriate selection of activating group A allows adjustment of the conditions required for aromatization. For example, when the activating group is a 2-pyridyl moiety, N-(2-pyridyl)-4-halotetrahydrophthalimide (X)

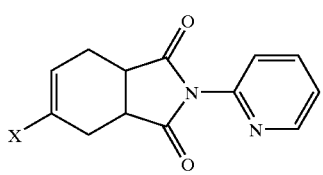

(X)

will readily aromatize in air in the presence of a catalyst to yield N-(2-pyridyl)-4-halophthalimide (XI)

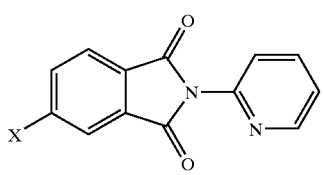

(XI)

This aromatization may be conducted in an inert solvent such as toluene, trichlorobenzene, or o-dichlorobenzene in the presence of a catalyst comprising a copper based compound such as CuO, $Cu_2O$, CuCl, $CuCl_2$, Cu (Acetylacetonate) (Cu (Acac)), and $CuCO_3Cu(OH)_2$. It is preferred for the catalyst to comprise both activated carbon and a copper based compound. An example of a catalyst comprising both activated carbon and a copper based compound is Calgon S-Sorb (an activated carbon comprising approximately 12% by weight $Cu_2O$), available from Calgon Corporation of Pittsburgh Pennsylvania. The amount of catalyst employed is determined by the type of catalyst, but generally the Cu compound is present in an amount of about 5–55 mol % based on the amount of activated 4-halotetrahydrophthalimide. The aromatization reaction is maintained at reflux conditions for about 3 to about 10 hours. The catalyst may be recycled but reactions using recycled catalyst may need to reflux for a longer period of time to achieve the same yield. Formation of the activated 4-halotetrahydrophthalimide and aromatization can be performed as a single step or as two sequential steps. When performed as sequential steps the activated 4-halotetrahydrophthalimide may be purified, if desired, by any method known in the art such as melt recrystallization, fractional distillation or column chromatography.

N-substituted-4-halo-phthalimide (V) may then be treated with the disodium salt of a dihydroxy compound having the formula (XII):

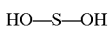

(XII)

wherein S is a divalent radical, for example a straight or branched chain alkylene group having from about 2 to about 20 carbon atoms; a cycloalkylene group having from about 3 to about 20 carbon atoms; or an arylene group having from 6 to about 20 carbon atoms, and halogenated derivatives thereof. The alkylene, cycloalkylene, and arylene groups may be further substituted with alkyl, halogenated alkyl, fluoro, alkoxy, nitro, phenyl, phenoxy, aryl or other groups, provided that such substitutions do not interfere with synthesis or reaction.

A particularly preferred dihydroxy compound is bis (phenol) (XIII):

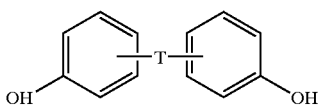

(XIII)

wherein T is a single bond linking the two aryl groups, or a divalent radical, for example a straight or branched chain alkylene group having from about 2 to about 20 carbon atoms; a cycloalkylene group having from about 3 to about 20 carbon atoms; or an arylene group having from 6 to about 20 carbon atoms, and halogenated derivatives thereof. The alkylene, cycloalkylene, and arylene groups may be further substituted alkyl, halogenated alkyl, fluoro, alkoxy, nitro, phenyl, phenoxy, aryl or other groups, provided that such substitutions do not interfere with synthesis or reaction. T further includes divalent functional groups such as sulfide, carbonyl, sulfoxide, and ether.

Illustrative examples of bis(phenol)s of formula (XI) include 2,2-bis(4-hydroxyphenyl)propane; 4,4'-bis(4-hydroxyphenyl)diphenyl ether; 4,4'-bis(4-phenoxy)diphenyl sulfide; 4,4'-bis(4-hydroxyphenyl)benzophenone ; 4,4'-bis (4-hydroxyphenyl)diphenyl sulfone; 2,2-bis(4-(3-hydroxyphenyl)phenyl)propane; 4,4'-bis(3-hydroxyphenyl) diphenyl ether; 4,4'-bis(3-hydroxyphenyl)diphenyl sulfide; 4,4'-bis(3-hydroxyphenyl)benzophenone; 4,4'-bis(3-hydroxyphenyl)diphenyl sulfone; 4-(3-hydroxyphenyl)-4'-(4-hydroxyphenyl)diphenyl-2,2-propane; 4-(3-hydroxyphenyl)-4'-(4-hydroxyphenyl)diphenyl ether; 4-(3-hydroxyphenyl)-4'-(4-hydroxyphenyl)diphenyl sulfide; 4-(3-hydroxyphenyl)-4'-(4-hydroxyphenyl) benzophenone, and 4-(hydroxyphenyl)-4'-(4-hydroxyphenyl)diphenyl sulfone dianhydride, as well as various mixtures thereof. A preferred bisphenol is bisphenol A. These and other bis (phenol)s and dihydroxy compounds are described in U.S. Pat. Nos. 3,972,902 and 4,455,410, which are incorporated herein by reference.

Reaction of N-substituted-4-halophthalimide (V) with the disodium salt of the dihydroxy compound (X) yields activated bisimides having the formula (VI):

(VI)

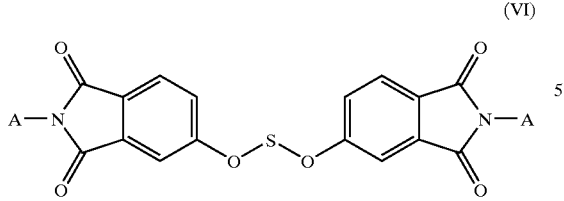

wherein A and S are as defined as above. The product of the reaction of (V) with the bis(phenol) (XIII) is activated bisimide (XIV))

(XIV)

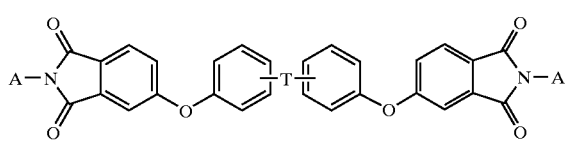

wherein A and T are as defined above.

In general the reaction of N-substituted-4-halophthalimide (V) with the disodium salt of bis(phenol) (XIII) or the disodium salt of dihydroxy compound (XII) may be effected by combining the disodium salt of the bis(phenol) dihydroxy compound with the N-substituted-4-halophthalimide (V) in the presence of a phase-transfer agent, as disclosed in U.S. Pat. No. 5,830,974 and U.S. Pat. No. 5,229,482. The reaction may be conducted in the melt phase, or in an inert solvent such as ortho-dichlorobenzene, meta-xylene and the like. Effective temperatures are in the range of about 100° C. to about 200° C. with about 120° C. to about 180° C. preferred. Other suitable methods for reaction of a disodium salt of bisphenol or dihydroxy compound with N-substituted-4-halophthalimide (V) are disclosed in U.S. Pat. Nos. 3,850,965; 4,827,000; 5,185,451; 4,868,316; 4,960,905; and 5,266,678.

The presence of activating group A in activated bisimide (VI) allows the direct reaction of activated bisimide (VI) with diamine (VII) to produce poly(etherimide) and the activating amine which can then be recycled. Diamine (VII) has the structure $H_2N-Z-NH_2$     (VII)

wherein Z is a divalent radical, for example a straight or branched chain alkylene group having from about 2 to about 20 carbon atoms; a cycloalkylene group having from about 3 to about 20 carbon atoms; or an arylene group having from 6 to about 20 carbon atoms, and halogenated derivatives thereof. The alkylene, cycloalkylene, and arylene groups may be further substituted with alkyl, aryl groups or other functional groups, provided that such substitutions do not interfere with synthesis of bisimide (VI) or any further reaction of bisimide (VI). Z further includes divalent, diarylene radicals of the following general formula (XV):

(XV)

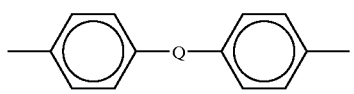

wherein Q includes, but is not limited to, the formula (XVI):

(XVI)

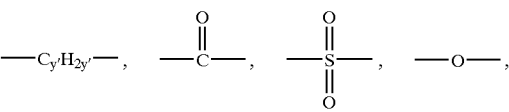

and   —S— wherein y is an integer from about 1 to about 5. Preferred alkylene groups include but are not limited to methylene, ethylene, propylene, isopropylene, n-butylene, and the like. Preferred arylene groups include but are not limited to 1,3-phenylene, naphthylene, and the like. A preferred Z group is 1,3-phenylene.

This polymerization via transimidization may be conducted in an inert solvent such as toluene, ortho dichlorobenzene, chlorobenzene or xylene at a temperature in the range from about 200 to about 300° C., and preferably in the range from about 225 to about 275° C. Preferably the reaction is run in an inert atmosphere. Polymerization via transimidization may also occur in the melt phase.

Alternatively, activated bisimide (VI) (or (XIV)) may be treated with a phthalic anhydride or subjected to hydrolysis ring closure to yield dianhydride (VIII):

(VIII)

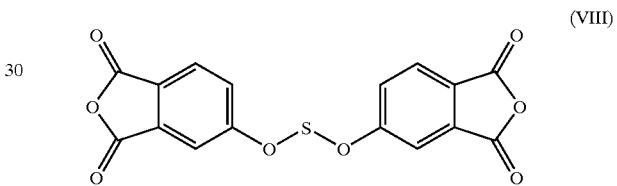

Dianhydride (VIII) may then be reacted with diamine (VII) to yield poly(etherimide).

Hydrolysis ring closure comprises treating the activated bisimide (VI) or (XIV) with strong base (caustic) to result in the tetra sodium salt which is then acidified to the tetra acid which, when heated or treated with acetid anhydride yields the dianhydride (VIII). Hydrolysis ring closure is typically performed in an inert solvent with a sufficient amount of caustic (strong base) to form the tetra sodium salt. The strength of the base is typically determined by the identity of the activating group A.

In another embodiment N-substituted-4-halophthalimide (V) can be reacted with diamine (VII) to produce the dihalobisimide (IX)

(IX)

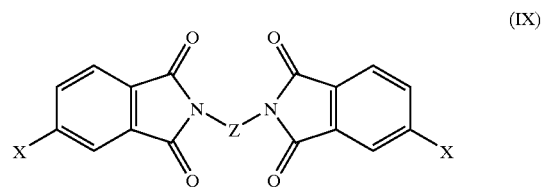

The reaction of 4-halophthalimide (V) with diamine (VII) is a transimidization reaction that is facilitated by the presence of the activating group A. Dihalobisimide (IX) can be reacted with the disodium salt of dihydroxy compound (XII) to yield poly (etherimide). Conditions for this reaction are taught in U.S. Pat. No. 5,229,482 to Brunelle.

All patents cited herein are incorporated by reference.

The invention is further described by the following non-limiting examples:

EXAMPLES

Example 1

Synthesis of N-(2-pyridyl)-4-Chlorotetrahydrophthalimide 119.5 grams (0.64 moles) of 4-chlorotetrahydrophthalic anhydride and 94.1 grams (0.64 moles) of 2-aminopyridine were added to a 500-mL, 3-necked, round-bottomed flask equipped with a Dean-Stark trap topped with a condenser, a nitrogen outlet, means for maintaining a mild sweep of nitrogen over the reaction mixture, and a magnetic stir. The material was heated to 130° C. with an externally heated oil bath to provide an easily stirred melt. The reaction was heated to 175° C. for a 45 minute period. The water of imidization collected in the Dean-Stark trap. The reaction was then heated to 220 to 225° C. for 2.5 hours and the resulting amber material was transferred into a clean glass jar. The crude material was recovered in 97% yield. HPLC analysis of the crude material indicated >98% purity of the desired compound.

Example 2

Synthesis of N-(2-pyridyl)-4-chlorophthalimide 6.0 grams (23.2 mmol) of N-(2-pyridyl)-4-chlorotetrahydrophthalimide, 37.4 milliliters of 1,2,4-trichlorobenzene, and 5.97 grams of Calgon carbon S-Sorb 12 30 mesh) was added to a 50-mL, round-bottomed flask, equipped with a reflux condenser, a magnetic stir bar, and a tube to deliver air below the surface of the reaction mixture. The reaction mixture was stirred and heated to reflux. Air was gently bubbled into the reaction mixture. The reaction was analyzed by HPLC after 2.5 hours and it was found that the desired product, N-(2-pyridyl)-4-chlorophthalimide, was formed in 88% yield. For comparison a similar experiment was run using 2 grams of N-methyl-4 chlorotetrahydrophthalimide and 4 grams of Calgon carbon S-Sorb. After 3 hours a 39% yield of the aromatized product was obtained. This result clearly demonstrates this importance of the activating group. The reaction of 4-chlorotetrahydrophthalic anhydride in the presence of Calgon carbon S-Sorb result only in minimal aromatization (about 0.5%).

Examples 3–8

Comparison of Catalysts in the Synthesis of N-(2-pyridyl)-4-chlorophthalimide 0.5 grams of N-(2-pyridyl)-4-chlorotetrahydrophthalimide and 4 milliliters of trichlorobenzene were combined with the catalysts shown in Table 1 in test tubes open to the air. The reaction mixtures were heated to 210° C. for 3 hours. Yield was determined by gas chromatography-mass spectrometry (GC-MS). Results are shown in Table 1. [t1]

TABLE 1

| Example | Catalyst | Amount of catalyst (grams) | Yield |
|---|---|---|---|
| 3 | Calgon S-Sorb | 0.5 | 51% |
| 4 | $Cu_2O$ | 0.1 | 4% |
| 5 | CuCl | 0.1 | 15% |
| 6 | $CuCl_2$ | 0.1 | 41% |
| 7 | Cu(Acac) | 0.1 | 27% |
| 8* | None | — | 0.5% |

*Comparative example

As can be seen from the preceding unoptimized examples, several copper based compounds are useful for catalyzing the aromatization of N-(2-pyridyl)-4-chlorophthalimide.

Examples 9–13

Comparison of Catalysts in the Synthesis of N-(2-pyridyl)-4-chlorophthalimide and N-phenyl-4-chlorophthalimide 0.2 grams of N-(2-pyridyl)-4-chlorotetrahydrophthalimide, 0.2 grams of N-(phenyl)-4-chlorotetrahydrophthalimide and 4 milliliters of trichlorobenzene were combined with the catalysts shown in Table 2 in test tubes open to the air. The reaction mixtures were heated to 210° C. for 4 hours. Yield was determined by gas chromatography-mass spectrometry (GC-MS). Results are shown in Table 2. [t2]

TABLE 2

| Ex. | Catalyst | Amount of catalyst (grams) | Yield of N-phenyl-4-chloro-phthalimide | Yield of N-(2-pyridyl)-4-chlorophthalimide |
|---|---|---|---|---|
| 9 | Calgon S-Sorb | 0.5 | 18.6% | 89.9% |
| 10 | $CuCO_3Cu(OH)_2$ | 0.1 | 1.8% | 69.7% |
| 11** | $CuCl_2$ | 0.1 | 5.8% | 62.9% |
| 12 | Cu(Acac) | 0.1 | 1.3% | 44.5% |
| 13* | None | — | 0% | 1.4% |

*Comparative example
**Example showed 10% dechlorination

As can be seen from Examples 9–12, 2-pyridyl is a more effective activating group than phenyl. Additionally, N-(2-pyridyl)-4-chlorotetrahydrophthalimide may be aromatized in the presence of a variety of copper based catalysts.

Example 14

One Step Synthesis of N-(2-pyridyl)-4-chlorophthalimide 5.2 grams of 4-chlorotetrahydrophthalic anhydride, 2.6 grams of 2-aminopyridine, 50 milliliters of trichlorobenzene and 6.0 grams of Calgon Carbon S-Sorb was combined in a 3 neck flask. The flask was fitted with a reflux condenser and an inlet tube adjusted to deliver air as bubbles below the surface. The third neck was fitted with a drying tube to remove water. After about 9 hours, N-(2-pyridyl)-4-chlorophthalimide was formed in about 84% yield as determined by GC-MS.

Example 15

Synthesis of Activated Bisimide

An appropriately sized oil jacketed vessel is charged with 1 mole of bisphenol A and water. The flask is flushed with nitrogen. Two moles of sodium hydroxide are added to the mixture, to afford a solution containing 15% solids. The reaction mixture is heated to 90° C. to afford a clear solution of BPA disodium salt. The aqueous salt is then dripped into refluxing toluene under an atmosphere of nitrogen over a three hour period in an appropriately sized oil jacketed vessel. Toluene and water are removed from the flask as the salt solution is added. Fresh toluene is added to the reaction vessel to maintain level. The disodium salt precipitates in the toluene. The final concentration of salt in the toluene slurry at the end of the addition is 20% by weight. Toluene is then stripped from the vessel as fresh dry toluene is added to maintain level (and thus % solids) in the vessel. Toluene is stripped over a period of 4 hours. At this point the salt is dry enough to react with the substrate.

2600 milliliters of dry toluene and 2 moles of dry 4-Chloro-N-(2-pyridyl) phthalimide are added to a oil jacketed vessel. The toluene solution is brought to 100° C. and 1 mol % (with respect to the amount of the salt) of hexaethylguanidium bromide is added to the vessel. The toluene solution is then brought to reflux and milliliters of toluene is removed from the vessel to assure that the reaction mixture is dry.

The bisphenol disodium salt is then slowly added to the solution of the imide and hexaethylguanidium bromide in toluene. The reaction is allowed to run for 2 hours with mechanical stirring under nitrogen at reflux. The percentage of solids is not allowed to go above 25%.

The reaction is cooled to 82° C. and contacted with 1% sodium hydroxide (organic phase to aqueous phase of 5:1, vol:vol) for 5 minutes with rapid stirring. The phases are allowed to separate and the aqueous phase is removed. This procedure is repeated. The organic phase contains the bisimide. The solvent is removed from the organic phase to afford the bisimide.

Example 16

Reaction of Activated Bisimide with 1,3-Diaminobenzene 50 milliliter side armed test tube was charged with 10.0 grams of an activated bisimide (XVII)

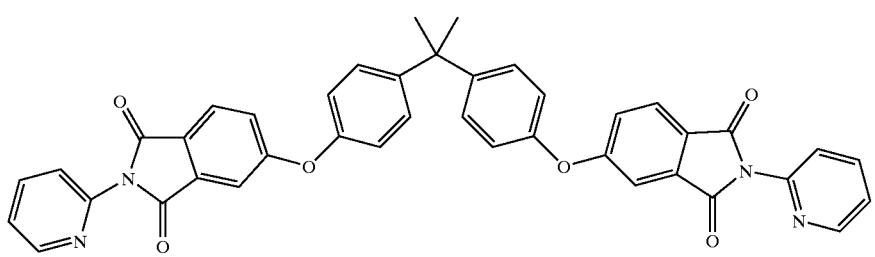

(XVII)

with an equimolar amount of metaphenylene diamine. The tube was heated at 270° C. for 50 minutes under a nitrogen atmosphere. The temperature was gradually raised to 310° C. as a vacuum was applied. The tube was then maintained at 310° C. for 1 hour. 2-aminopyridine was removed and trapped as the polyetherimide was formed.

Example 17

Reaction of N-(2-pyridyl)-4-chlorophthalimide and 1,3-metaphenylene Diamine

An oil-jacketed reactor is charged with 1 mole N-(2-pyridyl)-4-chlorophthalimide and 2500 grams of ortho-dichlorobenzene and 0.5 moles of metaphenylene diamine. The reactor is heated to reflux for 3 hours, and then placed under 5 to 15 psi nitrogen pressure. The reaction mixture is heated to 220° C. and the ortho-dichlorobenzene and 2-aminopyridine are allowed to distill overhead across a backpressure control valve. The dichloro bisimide product precipitates from the reaction mixture. Dry ortho-dichlorobenzene is added to the vessel at the same rate as it is lost via distillation. When precipitation stops the material is allowed to cool and the dichloro bisimide is isolated by filtration.

Example 18

Hydrolysis Ring Closure of Activated Bisimide (XVII) to Form Dianhydride 10 grams (14.88 millimoles) of activated bisimide (XVII), 5.95 grams (74.4 millimoles) if 50% by weight aqueous sodium hydroxide and 100 grams of water is added to a flask. A surfactant such as Triton X or methanol may be added to facilitate the hydrolysis reaction. The mixture is stirred at 160° C. under approximately 0.5 to 0.7 MegaPascals of pressure for 2 to 4 hours to form the tetra sodium salt. The tetra sodium salt mixture is then added slowly (over about 30 minutes), with stirring, to a flask containing 8.18 grams (81.84 millimoles) of 98% by weight sulfuric acid and 50 milliliters of water at 90 to 95° C. The mixture is refluxed for 1 hour and the pH is maintained below 1. The tetra acid precipitates from the reaction mixture and is collected by filtration. The tetra acid is then combined with 100 grams of xylene and brought to reflux to dry the tetra acid. The water and some xylene is collected in a Dean Stark receiver. Additions of xylene keep the amount of xylene constant. When no more water can be seen collecting in the Dean Stark receiver, 5.3 grams (52.1 millimoles) of acetic anhydride is added to complete the conversion of the tetra acid to the corresponding dianhydride. The mixture is refluxed for about 2 hours, filtered and allowed to cool. The dianhydride crystallizes from solution and is collected by filtration.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for the synthesis of an activated bisimide, comprising reacting 4-halotetrahydrophthalic anhydride with a primary amine having the formula A-NH$_2$ to yield an N-substituted-4-halotetrahydrophthalimide wherein A is a group which activates the tetrahydrophthalimide ring system to aromatization;

aromatizing activated 4-halotetrahydrophthalimide in the presence of a catalyst to yield an activated 4-halophthalimide; and treating activated 4-halophthalimide (V) with a disodium salt of a dihydroxy compound having the structure HO—S—OH, to yield the activated bisimide (VI):

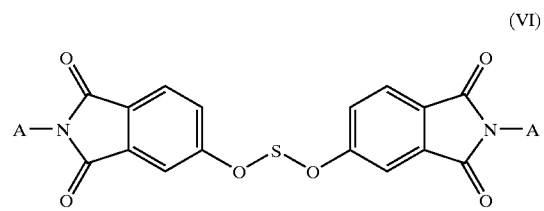

(VI)

wherein S comprises a straight or branched chain alkylene group having from about 2 to about 20 carbon atoms, a substituted straight or branched chain alkylene group having from about 2 to about 20 carbon atoms, a cycloalkylene group having from about 3 to about 20 carbon atoms, a substituted cycloalkylene group having from about 3 to about 20 carbon atoms, an arylene group having from 6 to about 20 carbon atoms or a substituted arylene group having from 6 to about 20 carbon atoms.

2. The method of claim 1, wherein S is selected from the group consisting of a straight or branched chain alkylene group having from about 2 to about 20 carbon atoms, a cycloalkylene group having from about 3 to about 20 carbon atoms, an arylene group having from 6 to about 20 carbon atoms, halogenated derivatives of arylene groups having from about 6 to 20 carbons.

3. The method of claim 1, wherein the dihydroxy compound is a bis(phenol) having the formula (XIII):

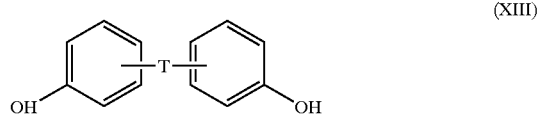

(XIII)

wherein T is selected from the group consisting of a single bond linking the two aryl groups, a straight or branched chain alkylene group having from about 2 to about 20 carbon atoms, a cycloalkylene group having from about 3 to about 20 carbon atoms; an arylene group having from 6 to about 20 carbon atoms, sulfide, carbonyl, sulfoxide, ether and mixtures thereof.

4. The method of claim 3, wherein T is selected from the group consisting of 2,2-bis[4-hydroxyphenyl]propane; 4,4'-bis(4-hydroxyphenyl)diphenyl ether; 4,4'-bis(4-phenoxy)diphenyl sulfide; 4,4'-bis(4-hydroxyphenyl)benzophenone; 4,4'-bis(4-hydroxyphenyl)diphenyl sulfone; 2,2-bis[4-(3-hydroxyphenyl) phenyl]propane; 4,4'-bis(3-hydroxyphenyl)diphenyl ether; 4,4'-bis(3-hydroxyphenyl)diphenyl sulfide; 4,4'-bis(3-hydroxyphenyl)benzophenone; 4,4'-bis(3-hydroxyphenyl)diphenyl sulfone; 4-(3-hydroxyphenyl)-4'-(4-hydroxyphenyl)diphenyl-2,2-propane; 4-(3-hydroxyphenyl)-4'-(4-hydroxyphenyl)diphenyl ether; 4-(3-hydroxyphenyl)-4'-(4-hydroxyphenyl)diphenyl sulfide; 4-(3-hydroxyphenyl)-4'-(4-hydroxyphenyl)benzophenone, and 4-(hydroxyphenyl)-4'-(4-hydroxyphenyl)diphenyl sulfone dianhydride, and mixtures thereof.

5. The method of claim 3, wherein the dihydroxy compound is bisphenol A.

6. The method of claim 1, wherein A is selected from the group consisting of pyridine, chloropyridine, nitropyridine, pyrimidine, pyrazine, thiazole, methylthiazole, benzothiazole, 1,3,4-thiadiazole, and benzotriflouride.

7. The method of claim 1, wherein A is 2-pyridyl.

8. The method of claim 1, wherein the catalyst is copper based.

9. The method of claim 8, wherein the catalyst further comprises activated carbon.

10. A method for the synthesis of poly(etherimide)s, comprising
    reacting 4-halotetrahydrophthalic anhydride with a primary amine having the formula A-NH$_2$ to yield an N-substituted-4-halotetrahydrophthalimide wherein A is a group which activates the tetrahydrophthalimide ring system to aromatization;
    aromatizing N-substituted-4-halotetrahydrophthalimide in the presence of a catalyst to yield an N-substituted-4-halophthalimide; and
    treating N-substituted-4-halophthalimide with a disodium salt of a dihydroxy compound having the structure HO—S—OH, to yield the activated bisimide (VI);

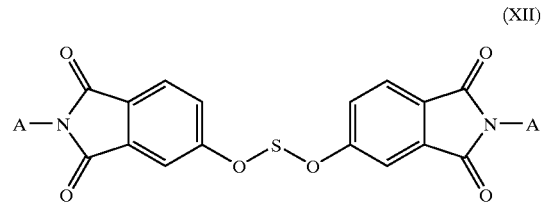

(XII)

wherein S comprises a straight or branched chain alkylene group having from about 2 to about 20 carbon atoms, a substituted straight or branched chain alkylene group having from about 2 to about 20 carbon atoms, a cycloalkylene group having from about 3 to about 20 carbon atoms, a substituted cycloalkylene group having from about 3 to about 20 carbon atoms, an arylene group having from 6 to about 20 carbon atoms or a substituted arylene group having from 6 to about 20 carbon atoms; and reacting activated bisimide (XII) with a diamine to form a poly(etherimide) and the primary amine.

11. The method of claim 10, wherein S is selected from the group consisting of a straight or branched chain alkylene group having from about 2 to about 20 carbon atoms, a cycloalkylene group having from about 3 to about 20 carbon atoms, an arylene group having from 6 to about 20 carbon atoms, halogenated derivatives of arylene groups having from about 6 to 20 carbons.

12. The method of claim 11, wherein the dihydroxy compound is a bis(phenol) having the formula (XIII):

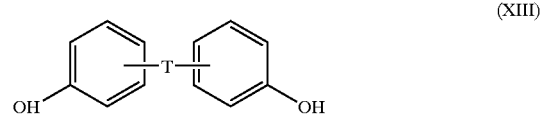

(XIII)

wherein T is selected from the group consisting of a single bond linking the two aryl groups, a straight or branched chain alkylene group having from about 2 to about 20 carbon atoms, a cycloalkylene group having from about 3 to about 20 carbon atoms; an arylene group having from 6 to about 20 carbon atoms, sulfide, carbonyl, sulfoxide, ether and mixtures thereof.

13. The method of claim 12, wherein the T is selected from the group consisting of 2,2-bis[4-hydroxyphenyl]propane; 4,4'-bis(4-hydroxyphenyl)diphenyl ether; 4,4'-bis(4-phenoxy)diphenyl sulfide; 4,4'-bis(4-hydroxyphenyl)benzophenone; 4,4'-bis(4-hydroxyphenyl)diphenyl sulfone; 2,2-bis[4-(3-hydroxyphenyl)phenyl]propane; 4,4'-bis(3-hydroxyphenyl)diphenyl ether; 4,4'-bis(3-hydroxyphenyl)diphenyl sulfide; 4,4'-bis(3-hydroxyphenyl)benzophenone; 4,4'-bis(3-hydroxyphenyl)diphenyl sulfone; 4-(3-hydroxyphenyl)-4'-(4-hydroxyphenyl)diphenyl-2,2-propane; 4-(3-hydroxyphenyl)-4'-(4-hydroxyphenyl)diphenyl ether; 4-(3-hydroxyphenyl)-4'-(4-hydroxyphenyl)diphenyl sulfide; 4-(3-hydroxyphenyl)-4'-(4-hydroxyphenyl)benzophenone, and 4-(hydroxyphenyl)-4'-(4-hydroxyphenyl)diphenyl sulfone dianhydride, and mixtures thereof.

14. The method of claim 10, wherein A is selected from the group consisting of pyridine, chloropyridine, nitropyridine, pyrimidine, pyrazine, thiazole, methylthiazole, benzothiazole, 1,3,4-thiadiazole, and benzotriflouride.

15. The method of claim 10, wherein A is 2-pyridyl.

16. The method of claim 10, wherein the diamine has the structure H$_2$N-Z-NH$_2$, wherein Z is selected from the group consisting of a straight or branched chain alkylene group having from about 2 to about 20 carbon atoms, a cycloalkylene group having from about 3 to about 20 carbon atoms, an arylene group having from 6 to about 20 carbon atoms, halogenated derivatives of an arylene group having from 6 to about 20 carbon atoms, and diarylene radicals of the following general formula (XV):

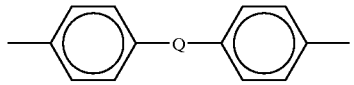
(XV)

wherein Q includes, but is not limited to, the formula (XVI):

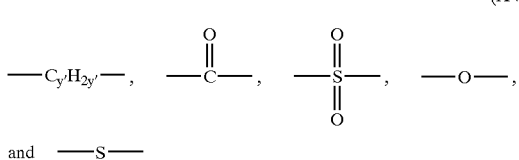
(XVI)

wherein y is an integer from about 1 to about 5, methylene, ethylene, propylene, isopropylene, n-butylene, 1,3-phenylene, naphthylene, and mixtures thereof.

17. The method of claim 10, wherein the catalyst is copper based.

18. The method of claim 17, wherein the catalyst further comprises activated carbon.

19. The method of claim 10 further comprising recycling the primary amine.

20. A method for the synthesis of poly(etherimide)s, comprising reacting 4-halotetrahydrophthalic anhydride with a primary amine having the formula A-NH$_2$ to yield an N-substituted-4-halotetrahydrophthalimide wherein A is a group which activates the tetrahydrophthalimide ring system to aromatization;

aromatizing the N-substituted-4-halotetrahydrophthalimide in the presence of a catalyst to yield an N-substituted-4-halophthalimide; and treating N-substituted-4-halophthalimide with a disodium salt of a dihydroxy compound having the structure HO—S—OH, to yield the activated bisimide (VI); and

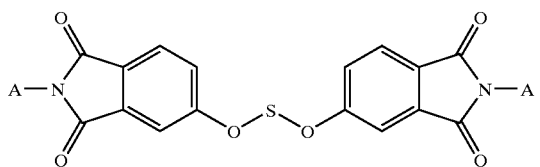
(VI)

converting the activated bisimide (VI) to dianhydride (VIII)

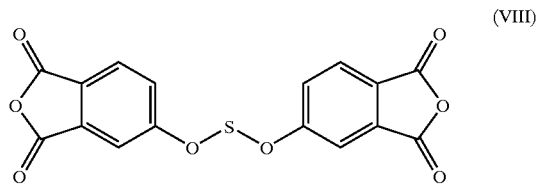
(VIII)

wherein S comprises a straight or branched chain alkylene group having from about 2 to about 20 carbon atoms, a substituted straight or branched chain alkylene group having from about 2 to about 20 carbon atoms, a cycloalkylene group having from about 3 to about 20 carbon atoms, a substituted cycloalkylene group having from about 3 to about 20 carbon atoms, an arylene group having from 6 to about 20 carbon atoms or a substituted arylene group having from 6 to about 20 carbon atoms and reacting dianhydride (VIII) with a diamine to yield a poly(etherimide).

21. The method of claim 20, wherein S is selected from the group consisting of a straight or branched chain alkylene group having from about 2 to about 20 carbon atoms, a cycloalkylene group having from about 3 to about 20 carbon atoms, an arylene group having from about 6 to about 20 carbon atoms, halogenated derivatives of arylene groups having from about 6 to 20 carbons.

22. The method of claim 20, wherein the dihydroxy compound is a bis(phenol) having the formula (XIII):

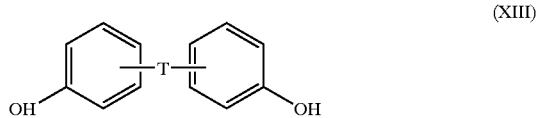
(XIII)

wherein T is selected from the group consisting of a single bond linking the two aryl groups, a straight or branched chain alkylene group having from about 2 to about 20 carbon atoms, a cycloalkylene group having from about 3 to about 20 carbon atoms; an arylene group having from 6 to about 20 carbon atoms, sulfide, carbonyl, sulfoxide, ether and mixtures thereof.

23. The method of claim 22, wherein T is selected from the group consisting of 2,2-bis[4-hydroxyphenyl]propane; 4,4'-bis(4-hydroxyphenyl)diphenyl ether; 4,4'-bis(4-phenoxy)diphenyl sulfide; 4,4'-bis(4-hydroxyphenyl) benzophenone; 4,4'-bis(4-hydroxyphenyl)diphenyl sulfone; 2,2-bis[4-(3-hydroxyphenyl)phenyl]propane; 4,4'-bis(3-hydroxyphenyl)diphenyl ether; 4,4'-bis(3-hydroxyphenyl) diphenyl sulfide; 4,4'-bis(3-hydroxyphenyl)benzophenone; 4,4'-bis(3-hydroxyphenyl)diphenyl sulfone; 4-(3-hydroxyphenyl)-4'-(4-hydroxyphenyl)diphenyl-2,2-propane; 4-(3-hydroxyphenyl)-4'-(4-hydroxyphenyl) diphenyl ether; 4-(3-hydroxyphenyl)-4'-(4-hydroxyphenyl) diphenyl sulfide; 4-(3-hydroxyphenyl)-4'-(4-hydroxyphenyl)benzophenone, and 4-(hydroxyphenyl)-4'-(4-hydroxyphenyl)diphenyl sulfone dianhydride, and mixtures thereof.

24. The method of claim 20, wherein A is selected from the group consisting of pyridine, chloropyridine, nitropyridine, pyrimidine, pyrazine, thiazole, methylthiazole, benzothiazole, 1,3,4-thiadiazole, and benzotrifluoride.

25. The method of claim 20, wherein A is 2-pyridyl.

26. The method of claim 20, wherein the diamine has the structure H$_2$N-Z-NH$_2$, wherein Z is selected from the group consisting of a straight or branched chain alkylene group having from about 2 to about 20 carbon atoms, a cycloalkylene group having from about 3 to about 20 carbon atoms, an arylene group having from 6 to about 20 carbon atoms, halogenated derivatives of an arylene group having from 6 to about 20 carbon atoms, and diarylene radicals of the following general formula (XV):

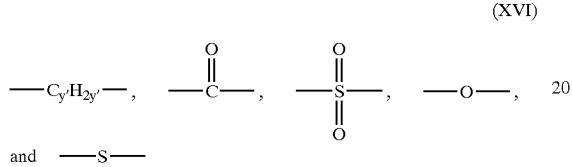

(XV)

wherein Q includes, but is not limited to, the formula (XVI):

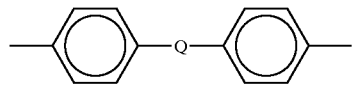

(XVI)

wherein y is an integer from about 1 to about 5, methylene, ethylene, propylene, isopropylene, n-butylene, 1,3-phenylene, naphthylene, and mixtures thereof.

27. The method of claim 20, wherein the activated bisimide (VI) is converted to dianhydride (VIII) by reacting the activated bisimide with phthalic anhydride.

28. The method of claim 20, wherein the activated bisimide (VI) is converted to dianhydride (VIII) by hydrolysis ring closure.

29. The method of claim 20, wherein the catalyst is copper based.

30. The method of claim 29, wherein the catalyst further comprises activated carbon.

31. A method for the synthesis of poly(etherimide)s, comprising reacting 4-halotetrahydrophthalic anhydride with a primary amine having the formula A-NH$_2$ to yield an N-substituted-4-halotetrahydrophthalimide wherein A is a group which activates the tetrahydrophthalimide ring system to aromatization;

aromatizing N-substituted-4-halotetrahydrophthalimide in the presence of a catalyst to yield an N-substituted-4-halophthalimide in the presence of a catalyst;

treating N-substituted-4-halophthalimide (V) with a diamine having the structure H$_2$N-Z-NH$_2$, wherein Z is selected from the group consisting of a straight or branched chain alkylene group having from about 2 to about 20 carbon atoms, a cycloalkylene group having from about 3 to about 20 carbon atoms, an arylene group having from 6 to about 20 carbon atoms, halogenated derivatives of an arylene group having from 6 to about 20 carbon atoms, and diarylene radicals of the following general formula (XV):

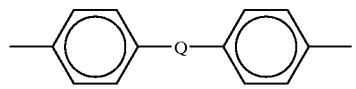

(XV)

wherein Q includes, but is not limited to, the formula (XVI):

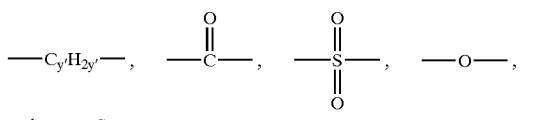

(XVI)

wherein y is an integer from about 1 to about 5 methylene, ethylene, propylene, isopropylene, n-butylene, 1,3-phenylene, naphthylene, and mixtures thereof to produce the dihalobisimide (IX); and

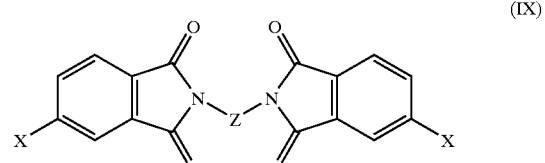

(IX)

reacting dihalobisimide (IX) with the disodium salt of a dihydroxy compound having the structure HO—S—OH wherein S comprises a straight or branched chain alkylene group having from about 2 to about 20 carbon atoms, a substituted straight or branched chain alkylene group having from about 2 to about 20 carbon atoms, a cycloalkylene group having from about 3 to about 20 carbon atoms, a substituted cycloalkylene group having from about 3 to about 20 carbon atoms, an arylene group having from 6 to about 20 carbon atoms or a substituted arylene group having from 6 to about 20 carbon atoms, to yield poly(etherimide).

32. The method of claim 31, wherein the catalyst is copper based.

33. The method of claim 32, wherein the catalyst further comprises activated carbon.

34. The method of claim 31, wherein A is selected from the group consisting of pyridine, chloropyridine, nitropyridine, pyrimidine, pyrazine, thiazole, methylthiazole, benzothiazole, 1,3,4-thiadiazole, and benzotriflouride.

35. The method of claim 34, wherein A is 2-pyridyl.

36. The method of claim 31, wherein the dihydroxy compound is bisphenol A.

37. A method for the synthesis of an activated 4-halophthalimide, comprising reacting 4-halotetrahydrophthalic anhydride with a primary amine having the formula A-NH$_2$ to yield an N-substituted-4-halotetrahydrophthalimide wherein A is a group which activates the tetrahydrophthalimide ring system to aromatization; and aromatizing activated 4-halotetrahydrophthalimide in the presence of a catalyst to yield an activated 4-halophthalimide.

38. The method of claim 37, wherein the catalyst is copper based.

39. The method of claim 38, wherein the catalyst further comprises activated carbon.

40. The method of claim 37, wherein A is selected from the group consisting of pyridine, chloropyridine, nitropyridine, pyrimidine, pyrazine, thiazole, methylthiazole, benzothiazole, 1,3,4-thiadiazole, and benzotriflouride.

41. The method of claim 40, wherein A is 2-pyridyl.

* * * * *